United States Patent [19]

Neubauer et al.

[11] Patent Number: 5,423,873
[45] Date of Patent: Jun. 13, 1995

[54] DEVICE FOR STIMULATING LIVING TISSUE

[75] Inventors: Heinz Neubauer, Jaerfaella; Jakub Hirschberg, Taeby; Hans Strandberg, Sundbyberg, all of Sweden

[73] Assignee: Siemens Elema AB, Solna, Sweden

[21] Appl. No.: 111,198

[22] Filed: Aug. 24, 1993

[30] Foreign Application Priority Data

Sep. 2, 1992 [SE] Sweden ............... 9202521

[51] Int. Cl.⁶ ............................................. A61N 1/36
[52] U.S. Cl. ........................................ 607/68; 607/30
[58] Field of Search ............... 607/7, 30, 32, 34, 59, 607/60, 66, 68

[56] References Cited

U.S. PATENT DOCUMENTS

| | | |
|---|---|---|
| 3,727,616 | 4/1923 | Lenzkes ............... 607/59 |
| 4,289,134 | 9/1981 | Bernstein . | 
| 4,459,989 | 7/1984 | Borkan ............... 607/66 X |
| 4,579,119 | 4/1986 | Callaghan . |
| 4,628,934 | 12/1986 | Pohndorf . |
| 4,877,032 | 10/1989 | Heinze et al. . |
| 4,989,602 | 2/1991 | Sholder et al. ............... 607/32 X |

Primary Examiner—Lee S. Cohen
Assistant Examiner—Jeffrey R. Jastrzab
Attorney, Agent, or Firm—Hill, Steadman & Simpson

[57] ABSTRACT

A device for stimulating heart tissue contains a stimulation unit connected via a switching device to an electrode system. The number of connecting lines between the stimulation unit and the switching device is minimized by emitting control signals and stimulation pulses from a common pulse signal output socket of the stimulation unit. The switching device contains a signal discriminator which separates the control signals from the stimulation pulses, the control signals then controlling the switching device such that the stimulation pulses are delivered to a specific part of the electrode system.

6 Claims, 3 Drawing Sheets

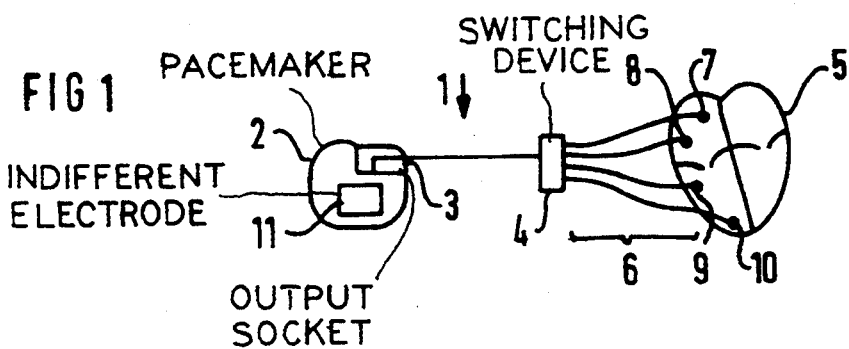
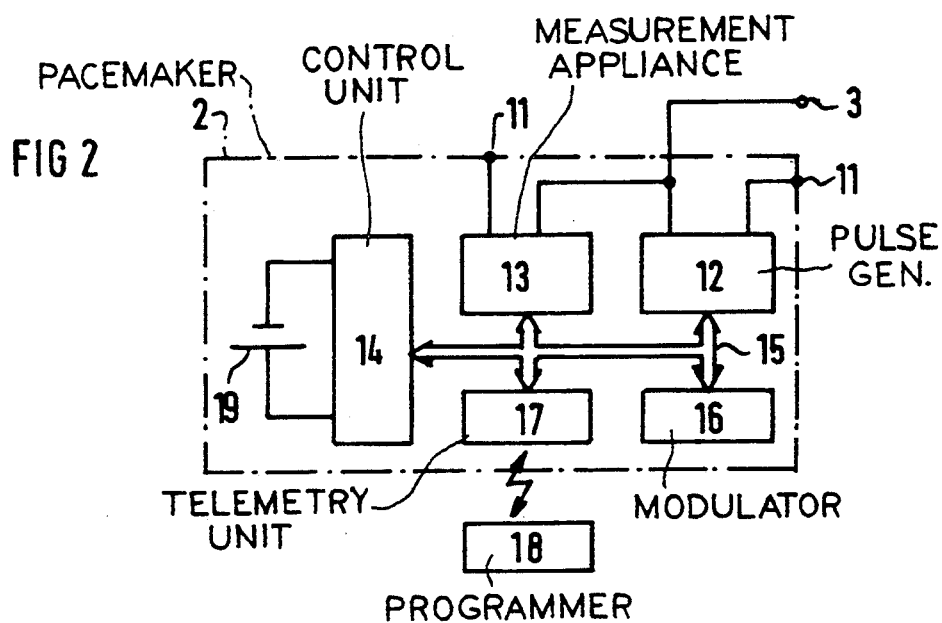
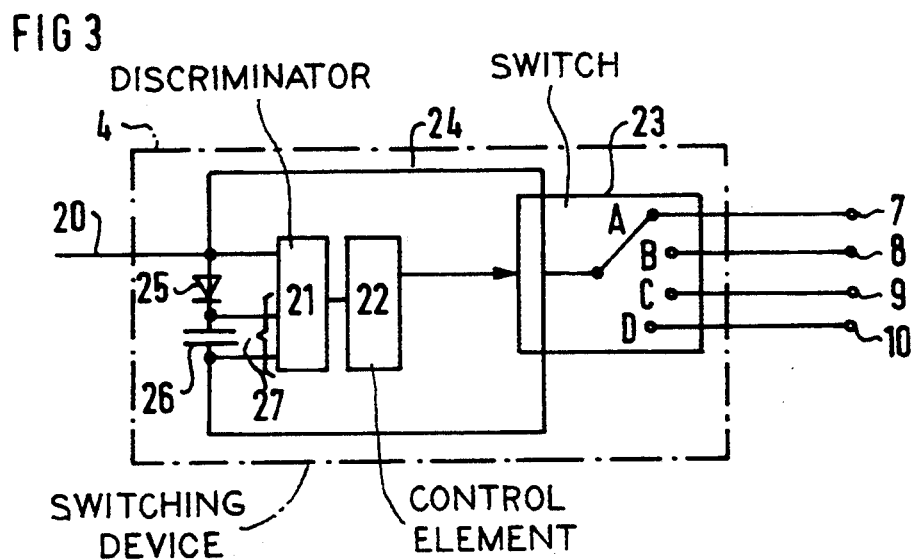

DEVICE FOR STIMULATING LIVING TISSUE

BACKGROUND OF THE INVENTION

1. Field of the Invention

The present invention relates to a device for stimulating living tissue, of the type having a stimulation unit which emits stimulation pulses from a pulse signal output socket, an electrode system which delivers the stimulation pulses to the living tissue, a controllable switching device connected between the electrode system and the pulse signal output socket for transmitting the stimulation pulses to a specific part of the electrode system, and a control device which emits control signals from a control output socket to a control input socket on the switching device to control the transmission of stimulation pulses.

2. Description of the Prior Art

A device of the type generally described above is disclosed in U.S. Pat. No. 4,628,934. This known device contains a pacemaker, a switching unit and an electrode system. The electrode system consists of two multipolar electrodes which can be unipolarly or bipolarly connected to the pacemaker via the switching unit. The switching unit is controllable, and is directly controlled from pacemaker electronic circuitry via control lines.

By means of the switching unit, the required number of feedthroughs to pacemaker electronic circuitry, which is enclosed in a pacemaker case, can be reduced. In a unipolar version, one feedthrough is employed for delivering stimulation pulses from pacemaker electronic circuitry and control lines for controlling the switching unit. In a bipolar version, there are two feedthroughs, each with a line for delivering stimulation pulses, and control lines to the switching unit. In one version of this known device, a serial-to-parallel signal converter is employed in the switching unit to reduce to one the number of control lines to the pacemaker electronic circuitry. A pulse train, which in the serial-to-parallel signal converter is applied in parallel to the switches in the switching unit, is then fed through this single control line. When the switching device is devised in the form of a detachable adapter for a pacemaker, two electrodes can be coupled, via the adapter, to a pacemaker designed for one electrode.

SUMMARY OF THE INVENTION

It is an object of the present invention to provide a device of the type generally described above in which the number of feedthroughs is further reduced.

It is a further object of the to provide such a device which can easily be adapted to a plurality of functions in, e.g., the diagnosis or therapeutic treatment of living tissue.

Such a device is achieved in accordance with the principles of the present invention having a control device with a control output socket which is coupled to the pulse signal output socket, switching device with a control input socket coupled to the pulse signal output socket, and wherein the switching device contains a signal discriminator to separate control signals from stimulation pulses so that the control signals control the transmission of the stimulation pulses to the tissue.

The number of feedthroughs is thereby minimized. For a unipolar device, one feedthrough is sufficient through which stimulation pulses and control signals are transmitted to the switching device and on to the electrode system. In the corresponding way, a bipolar device has two feedthroughs. The signal discriminator discriminates the different types of signals and separates them so the control signal can be used for controlling the setting of the switching device. In a version of the invention with a pacemaker, a plurality of electrodes can be placed in a heart and connected to the pacemaker via the switching device. The heart's response to stimulation pulses at different locations in the heart can be easily studied so as to, e.g., ascertain the best site for a permanently implanted electrode.

One way of discriminating stimulation pulses and control signals is achieved in accordance with the invention in an embodiment wherein the control signals and the stimulation pulses have different polarities, and the signal discriminator senses polarity in order to distinguish control signals from stimulation pulses.

The different polarities make it easy to distinguish between the types of signal. Regardless of whether the same or different polarities are used for the signals, it is advantageous for the control signals to have an amplitude lower than the threshold value required to stimulate the living tissue, since there would then be no risk of erroneous tissue stimulation caused by control signals misdirected to the electrode system.

Alternatively, the signals can be discriminated in an embodiment wherein the control device contains a modulator to modulate the stimulation pulses with the control signals, and the signal discriminator contains a demodulator to separate the control signals from the stimulation pulses.

In another embodiment of a device in accordance with the invention, at least one measurement device is coupled, via the switching device, to the pulse signal output socket, and the control device, by means of a control signal, closes a signal connection between the measurement device and a measurement appliance in the stimulation unit.

As a result, the device can be expanded into a multifunctional unit capable of stimulating tissue and measuring physiological variables in stimulated or other tissue. The measured variables can be used by the stimulation unit for enhanced monitoring and control of tissue stimulation. Physiological variables which can be measured are, e.g., temperature, blood oxygen, tissue impedance and movements. When the control signal closes the connection between the stimulation unit and the measurement device, the measurement signal is sent from the measurement device to the measurement appliance.

In this context, it is advantageous for the measurement device to be controllable, for which purpose the control device emits measurement control signals and the signal discriminator distinguishes between control signals for directing the stimulation pulses and measurement control signals. The measurement control signals control the transmission by the switching device of measurement control signals to the measurement device.

The stimulation unit then provides complete control over all functional units in the device. The control signals open different connections between the stimulation unit and the electrode system or the measurement device over the switching device. The stimulation unit can control the measurement device's measurement of the physiological variable, and also receives the measurement signals from the measurement device, in order to vary stimulation of the living tissue on the basis thereof.

In another embodiment of the device in accordance with the invention, the switching device contains a power supply input socket connected to the pulse signal output socket, and the stimulation unit contains a power source which delivers power to the power supply input socket.

In this way, the power requirements of the switching device are completely fulfilled by the stimulation unit. Power can be transmitted as a supply current to the power supply input socket in the switching device, or the switching device can contain a capacitor connected to the power supply input socket through, and the power source charges the capacitor.

One advantage in this context is that the power source is connected to the measurement device through the switching device, and the power source supplies current for the measurement device's power requirements when the connection between the power source and the measurement device is closed.

DESCRIPTION OF THE DRAWINGS

FIG. 1 is a schematic illustration of a first embodiment of a device constructed in accordance with the principles of the present invention.

FIG. 2 is a block diagram of the stimulation unit in the device of FIG. 1.

FIG. 3 is a block diagram of the switching device in the device of FIG. 1.

DESCRIPTION OF THE PREFERRED EMBODIMENTS

Figure 4:
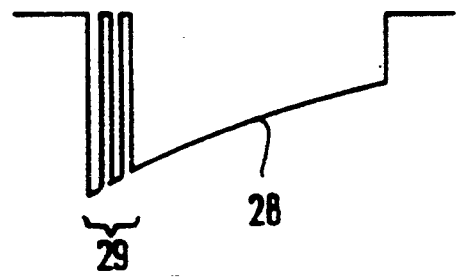
FIGS. 4–6 respectively illustrate three different ways of sending a control signal and a stimulation pulse from the stimulation unit to the switching device in the device of FIG. 1.

The device 1 in FIG. 1 has a stimulation unit in the form of a pacemaker 2 which is connected, through a socket 3 and a switching device 4, to a heart 5 by an electrode system 6. The stimulation unit 2 could be a defibrillator or a cardioverter (or a combination of such devices), but for simplicity will only be described henceforth as a pacemaker 2. The electrode system 6 consists of a first tip electrode 7 and a second tip electrode 8 placed in the atrium of the heart 5, a third tip electrode 9 and a fourth tip electrode 10 placed in the ventricle of the heart 5. The pacemaker 2 is unipolarly coupled and has an indifferent electrode 11 on the exterior of the pacemaker 2 to conduct stimulation pulses back to the pacemaker from the electrode system 6. A stimulation pulse is generated by the pacemaker 2 and sent, along with a control signal, to the switching device 4. The control signal changes the state of the switching device 4 in such a way that the stimulation pulse is sent to one of the tip electrodes 7–10 in the electrode system 6 and delivered to the heart 5. The stimulation pulse is then conducted over body tissue back to the indifferent electrode 11 and the pacemaker 2.

FIG. 2 shows a block diagram of the pacemaker 2, containing a pulse generator 12 connected to the pulse signal output socket 3 and the indifferent electrode 11, and a measurement appliance 13 which is also connected to the pulse signal output socket 3 and the indifferent electrode 11. The pulse generator 12 generates the stimulation pulses. The measurement appliance 13 senses the heart's electrical activity after the switching device 4 closes a connection between the pacemaker 2 and the electrode system 6. A control unit 14 controls the pulse generator 12 and the measurement appliance 13 via a data bus 15. Stimulation pulses can be modulated with control signals in a modulator 16. The modulator 16 is also connected to the control unit 14 via the data bus 15. Using a telemetry unit 17 and an extracorporeal programming unit 18, a physician can program the control unit 14 to perform various functions. The telemetry unit 17 is also connected to the data bus 15. Power for the pacemaker 2 is supplied by a battery 19.

Stimulation pulses with superimposed control signals are sent by the pulse generator 12 from the pulse signal output socket 3 to the switching device 4. In the switching device 4, as shown in FIG. 3, the signals in the switching device 4 are sent via a signal input socket 20 to a signal discriminator 21 which demodulates the control signal and feeds it to a control element 22 for controlling a switch 23. The switch 23 has four output positions 23A-D respectively connected to the first tip electrode 7, the second tip electrode 8, the third tip electrode 9 and the fourth tip electrode 10. A line 24 connects the switch 23 to the signal input socket 20 to transmit stimulation pulses across the switch 23 to the selected electrode tip. The switching device 4 also contains a diode 25 and a capacitor connected in parallel with the line 24 to drive the switching device 4. The diode 25 is connected to the signal input socket 20 and to the capacitor 26 which is connected across the power supply input socket 27 of the switching device 4. An energy pulse, having a polarity opposite to the polarity of the stimulation pulses, is emitted to charge the capacitor 26 with the energy required to drive the switching device 4.

Figure 5:
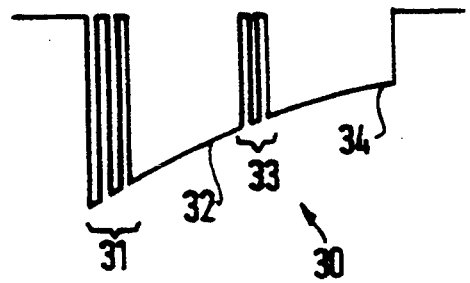
Figure 6:
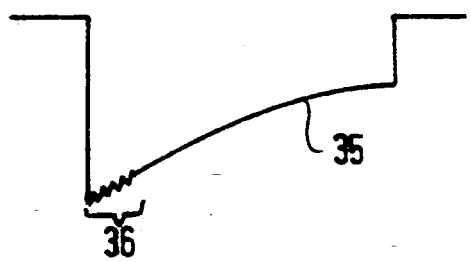

Referring to FIGS. 4–6, three examples of stimulation pulses which can be used in the device according to FIGS. 1–3 will be described below. FIG. 4 shows a first stimulation pulse 28 with a superimposed control signal 29. The stimulation pulse 28 is generated by the pulse generator 12 with an amplitude and duration controlled by the control unit 14. The modulator 16 modulates the control signal 29 over the first part of the stimulation pulse 28. The stimulation pulse 28 is sent from the pulse signal output socket 3 to the signal input socket 20 of the switching device 4. The control signal is demodulated in the signal discriminator and fed to the control element 22 which sends a switching signal to the switch 23. For example, if the pacemaker is to deliver a stimulation pulse to the atrium of the heart 5 via the first tip electrode 7, the control signal indicates that the switch 23 must enable output position 23A which is connected to the first tip electrode 7. The stimulation pulse 28 is thereby transmitted from the signal input socket 20 via line 24 to the switch 23 and through output position 23A to the first tip electrode 7, which delivers the stimulation pulse 28 to the heart 5. The stimulation pulse 28 is then conducted through body tissue back to the indifferent electrode 11 and the pulse generator 12.

FIG. 5 shows a second stimulation pulse 30 which contains a first control signal in the form of a pulse packet 31, a first stimulation pulse part 32, a second control signal in the form of a pulse packet 33 and a second stimulation pulse part 34. The first control signal 31 can, e.g., cause transmission of the first stimulation pulse part 31 to the heart 5 via the third tip electrode 9, and the second control signal 33 can set the switch 23 such that the second stimulation pulse part 34 is delivered to the heart 5 via the fourth tip electrode 10.

FIG. 6 shows a third stimulation pulse 35 in which the control signal 36 consists of a high-frequency signal 30, superimposed on the stimulation pulse 35.

Figure 7:
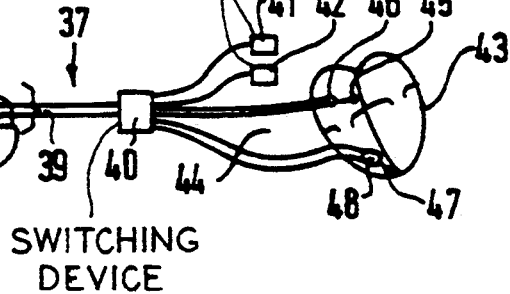
FIG. 7 is a schematic illustration of a second embodiment of a device constructed in accordance with the principles of the present invention.

A second embodiment of the device according to the invention is shown in FIG. 7. The device 37 includes a pacemaker 38 for bipolar operation which is connected, via a pulse signal output socket 39 and a switching device 40, to a first measurement device 41, a second measurement device 42 and, through an electrode system 44, to a heart 43. For unipolar operation, the pacemaker 38 has an indifferent electrode 49 on its case. The electrode system 44 includes a first tip electrode 45 and a first ring electrode 46 placed in the atrium of the heart 43, and a second tip electrode 47 and a second ring electrode 48 placed in the ventricle of the heart 43. A stimulation pulse generated by the pacemaker 38 and a control signal are simultaneously emitted and act on the switch 40 to complete a connection with, e.g., the second tip electrode 47, which delivers the stimulation pulse to the heart 43, and the second ring electrode 48, via which the stimulation pulse is conducted back to the pacemaker 38.

Figure 8:
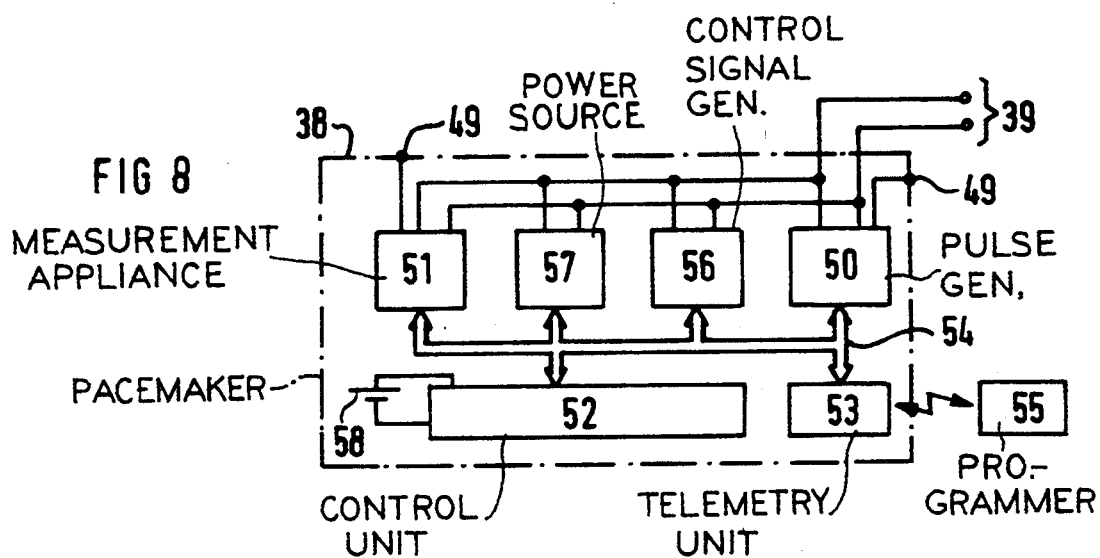
FIG. 8 is a block diagram of the stimulation unit in the device of FIG. 7.

As FIG. 8 shows, the pacemaker 38 contains, like the pacemaker 2 in FIG. 2, a pulse generator 50, a measurement appliance 51 (such as a signal evaluation unit, which may also transmit signals to the measurement devices 41 and 42), a control unit 52 and a telemetry unit 53, all connected to each other via a data bus 54. The telemetry unit 53 transmits programming and information data between the control device 52 and an extracorporeal programming unit 55. The pacemaker 38 also contains a control signal generator 56 and a power source 57, both connected to the pulse signal output socket 39. The pulse generator 50, the control-signal generator 56 and the power source 57 are shown as three separate units for clarity, but could consist of a single unit. All pacemaker electronic circuitry is supplied with power by the battery 58. With the control signal generator 56, the control device 52 controls the switching device 40 to connect the first measurement device 41 or the second measurement device 42 or any of the electrodes 45, 46, 47, 48 of the electrode system 44 to the pulse signal output socket 39.

Figure 9:
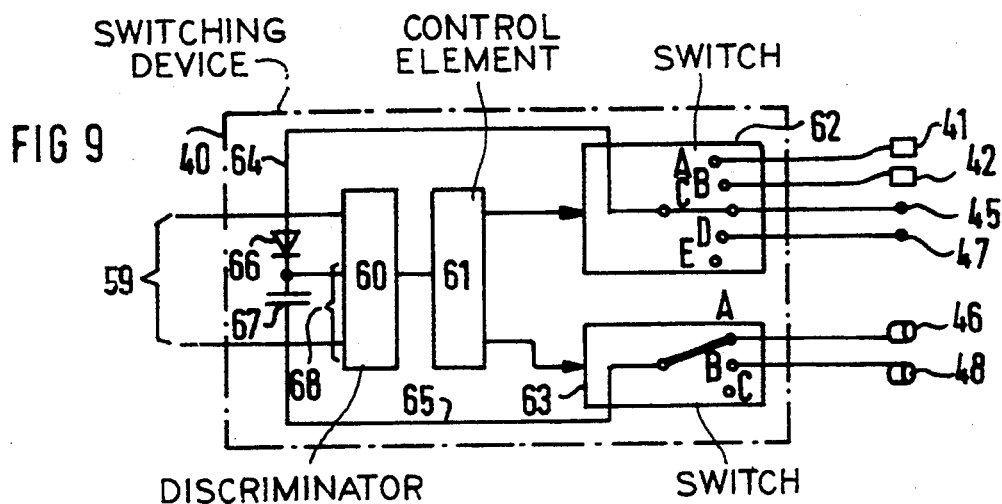
FIG. 9 is a block diagram of the switching device in the device of FIG. 7.

As shown in FIG. 9, the switching device 40 has a signal input socket 59 which is connected to the pulse signal output socket 39 and which conducts signals from the pulse signal output socket 39 to a signal discriminator 60 to separate the control signal and send it to a control element 61. The control element 61 controls a first switch 62 and a second switch 63. The first switch 61 has five output positions 62A-E, the first output position 62A connected to the first measurement device 41, the second output position 62B connected to the second measurement device 42, the third output position 62C connected to the first tip electrode 45 and the fourth output position 62D connected to the second tip electrode 47. The fifth output position 62E has no further connection. The second switch 63 has three output positions 63A-C, the first output position 63A connected to the first ring electrode 46, the second output position 63B connected to the second ring electrode 48, the third output position 63C having no further connection. A first line 64 connects the signal input socket 59 to the first switch 62, and a second line 65 connects the signal input socket 59 to the second switch 63.

A series-connected diode 66 and capacitor 67 are connected in parallel across the signal input socket 59, the capacitor 67 being charged from the pacemaker 38 in order to supply the switching device 40 with power through a power supply input socket 68.

Figure 10:
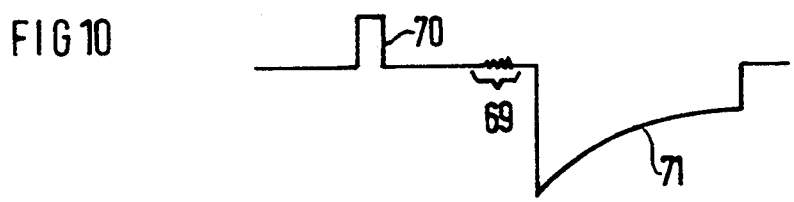
FIGS. 10–11 respectively illustrate two different ways of sending a plurality of different signals from the stimulation unit to the switching device in the device of FIG. 7.
Figure 11:
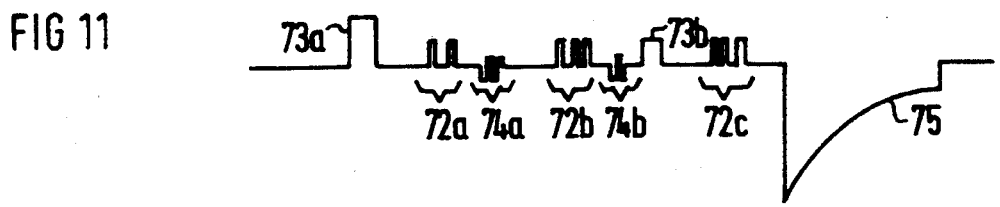

Referring to FIGS. 10 and 11, two examples of signal transmission which can be used in the device 37 according to FIG. 7-9 will be described below. FIG. 10 shows an energy pulse 70, generated by the power source 57, to charge the capacitor 67. The switching device 40 is in its output mode, i.e., the first switch 62 is in its fifth position 62E and the second switch 63 is in its third position 63C. A control signal 69 follows the energy pulse 70 and causes the first switch 62 to be set at its third position 62C in order to send the stimulation pulse 71 to the first tip electrode 45, and sets the second switch 63 to its first position 63A so as to conduct the stimulation pulse 71 back to the pulse generator 50 over the first ring electrode 46 and the switching device 40. The stimulation pulse 71 can also be emitted unipolarly, whereby the second switch 63 is set at its third output position 63C, and the connection between the indifferent electrode 49 and the pulse generator 50 is closed.

FIG. 11 shows a first energy pulse 73a for charging the capacitor 67. A first control signal 72a closes the connection between the measurement appliance 51 and the first measurement device 41, a measurement signal 74a then being transmitted from the first measurement device 41 to the measurement appliance 51. A second control signal 72b sets the switch 62 such that the connection to the second control device 42 is closed. The measurement appliance 57 emits a second energy pulse 73b followed by a measurement control signal 74b generated by the power source 57 in order to supply the second measurement device 42 with power and to control same. The second measurement device 42 may have a capacitor which is charged by the second energy pulse 73b. A third control signal 72d causes the connection with the second tip electrode 47 and the second ring electrode 48 to close so a stimulation pulse 75 is delivered to the heart 43.

The switches 23, 62, 63 in FIGS. 3 and 9 can be devised with, e.g., transistors or in some other known manner. Power for the switching device 40 can also be provided in some way other than with a capacitor 67 which is charged, viz. by having the power source 57 emit a supply current sufficient for the power requirements of the switching device 40.

Although modifications and changes may be suggested by those skilled in the art, it is the intention of the inventors to embody within the patent warranted hereon all changes and modifications as reasonably and properly come within the scope of their contribution to the art.

We claim as our invention:
1. A device for stimulating living tissue comprising:
   stimulation pulse generator means, having an output socket, for generating a stimulation signal having a polarity at said output socket;

electrode means having a plurality of stimulation signal delivery elements for transmitting said stimulation signal to different tissue sites;

control means, having a control means output connected to said output socket, for generating a control signal at said control means output, said control signal having a polarity opposite to the polarity of said stimulation signal and being superimposed on said stimulation signal at said output socket;

switching means, responsive to said control signal and having an input connected to said output socket which receives said stimulation signal with said control signal superimposed thereon and having outputs connected to said electrode means, for directing said stimulation signal to a selected tissue site, determined by said control signal, via at least one of said delivery elements; and discriminator means in said switching means for separating said control signal from said stimulation signal before directing said stimulation signal to said selected tissue site.

2. A device as claimed in claim 1 wherein said control means comprises means for generating said control signal with an amplitude lower than an amplitude capable of stimulating said living tissue.

3. A device as claimed in claim 1 wherein said control means comprises means for modulating said stimulation signal with said control signal to form a modulated signal and wherein said discriminator means comprises means for demodulating said modulated signal to separate said stimulation signal and said control signal.

4. A device as claimed in claim 1 wherein said switching means has a power supply input connected to said output socket, and wherein said stimulation pulse generator means includes a power source connected to said output socket for supplying power to said power supply input.

5. A device as claimed in claim 4 wherein said switching means draws a supply current, and wherein said power source supplies said supply current to said switching device through said output socket.

6. A device as claimed in claim 4 wherein said switching means includes a capacitor connected to said power supply input and to said electrode means, said power source charging said capacitor.

* * * * *